(12) United States Patent
Laskoski et al.

(10) Patent No.: US 8,039,576 B2
(45) Date of Patent: Oct. 18, 2011

(54) AROMATIC ETHER AND ALKYNYL CONTAINING PHTHALONITRILES

(75) Inventors: Matthew Laskoski, Springfield, VA (US); Teddy M Keller, Fairfax Station, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 353 days.

(21) Appl. No.: 11/850,854

(22) Filed: Sep. 6, 2007

(65) Prior Publication Data

US 2009/0069484 A1    Mar. 12, 2009

(51) Int. Cl.
*C08G 63/78*    (2006.01)
*C08G 67/02*    (2006.01)
*C08F 38/00*    (2006.01)

(52) U.S. Cl. ........ 528/205; 528/210; 528/392; 528/422; 528/425; 526/285

(58) Field of Classification Search .......... 524/607, 524/612, 430, 432, 496; 523/200, 222; 528/208, 528/362, 205, 206, 210, 392, 422, 425; 525/328.1, 525/377, 398, 538; 526/285
See application file for complete search history.

(56) References Cited

U.S. PATENT DOCUMENTS

| | | | | |
|---|---|---|---|---|
| 5,003,039 A | * | 3/1991 | Keller | 528/362 |
| 5,374,701 A | * | 12/1994 | Hay et al. | 526/285 |
| 5,464,926 A | * | 11/1995 | Keller | 528/206 |
| 5,965,268 A | * | 10/1999 | Sastri et al. | 428/408 |
| 6,756,470 B2 | | 6/2004 | Keller et al. | |
| 2008/0255287 A1 | * | 10/2008 | Laskoski et al. | 524/432 |

* cited by examiner

Primary Examiner — Vasu Jagannathan
Assistant Examiner — Hannah Pak
(74) Attorney, Agent, or Firm — Amy L. Ressing; Joseph T. Grunkemeyer

(57) ABSTRACT

Compounds having the formulas below. R is an aromatic-containing group. Each M is an alkali metal. Each m is a positive integer. The value of n is a positive integer. The value p is 0 or 1. If p is 0 then n is 1. A thermoset made by curing a composition containing the below phthalonitrile monomers.

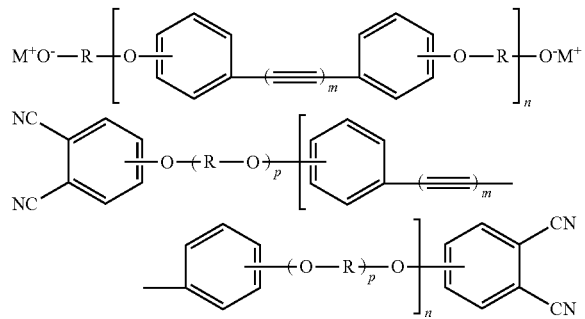

A method of reacting a diphenyl acetylene compound with an excess of an aromatic diol in the presence of an alkali metal carbonate to form the above oligomer. A method of reacting a phenoxyphthalonitrile with an acetylene compound to form the phthalonitrile monomer below.

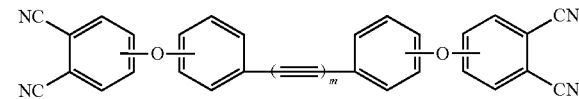

6 Claims, 3 Drawing Sheets

AROMATIC ETHER AND ALKYNYL CONTAINING PHTHALONITRILES

FIELD OF THE INVENTION

The invention is generally related to phthalonitriles.

DESCRIPTION OF RELATED ART

Phthalonitrile monomers and phthalonitrile polymers of various types are described generally in U.S. Pat. Nos. 3,730,946, 3,763,210, 3,787,475, 3,869,499, 3,972,902, 4,209,458, 4,223,123, 4,226,801, 4,234,712, 4,238,601, 4,259,471, 4,304,896, 4,307,035, 4,315,093, 4,351,776, 4,408,035, 4,409,382, 4,410,676, 5,003,039, 5,003,078, 5,004,801, 5,132,396, 5,159,054, 5,202,414, 5,208,318, 5,237,045, 5,242,755, 5,247,060, 5,292,854, 5,304,625, 5,350,828, 5,352,760, 5,389,441, 5,464,926, 5,925,475, 5,965,268, 6,001,926, 6,297,298, 6,756,470, 6,891,014, and U.S. Patent Application Publication Nos. 2004/0181027 and 2004/0181029. (All referenced patent documents and publications throughout this application are incorporated herein by reference.)

The above references generally teach methods for making and polymerizing phthalonitrile monomers. Such monomers typically have two phthalonitrile groups, one at each end of a connecting spacer chain. The monomers can be cured, whereby the cross-linking occurs between cyano groups. These cross-linked networks typically have high thermal and oxidative stability.

Phthalonitrile resins have potential as matrix materials for advanced composites for radome, airframe, missile, and electronic applications. Phthalonitrile monomers polymerize through the cyano groups with the aid of an appropriate curing agent to yield a crosslinked polymeric network with high thermal and oxidative stabilities. These polymers are obtained by heating the phthalonitrile monomers and a small amount of curing additive in the melt-state for extended periods of time at elevated temperatures. A variety of phthalonitrile monomers containing aromatic ether, thioether, imide, and sulfone linkages between the terminal phthalonitrile units have been synthesized and cured or converted to crosslinked/networked polymers. The cure reaction of these monomers has been investigated by a variety of curing additives such as organic amines, strong organic acids, strong organic acids/amine salts, metallic salts, and metals. When postcured at elevated temperatures to about 400° C., the thermosets show long-term thermal and oxidative stabilities to temperatures approaching 375° C. In addition, the high aromatic content of the thermoset affords a high char yield (80-90%) when pyrolyzed to 1000° C. under inert conditions. The high thermal stability and the ability to form a high char yield upon pyrolysis contribute to the outstanding fire performance of phthalonitrile polymers. For instance, the fire performance of phthalonitrile-carbon and phthalonitrile-glass composites are superior to that of other thermoset-based composites currently in use for aerospace, ship and submarine applications. The phthalonitriles are still the only polymeric material that meets MIL-STD-2031 for usage inside of a submarine.

Low melting oligomeric phthalonitrile monomers and curing additives that do not volatilize at elevated cure reaction temperatures such as bis[4-(4-aminophenoxy)phenyl]sulfone (p-BAPS) have been shown to enhance the overall physical properties and processability of phthalonitrile-based composites. Most high temperature resins are not amenable to processing by cost effective methods such as RTM, resin infusion molding, and oven cure due to high initial viscosities, the evolution of volatiles during the cure, and or solvent-related problems.

SUMMARY OF THE INVENTION

Disclosed is a compound having the formula below. Each R is an independently selected aromatic-containing group. Each M is an alkali metal. Each m is an independently selected positive integer. The value of n is a positive integer.

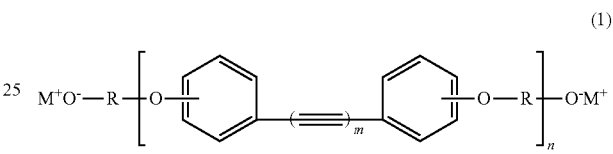

Also disclosed is a phthalonitrile monomer having the formula below. R, m, and n are as defined above. The value of p is 0 or 1, with the proviso that if p is 0 then n is 1.

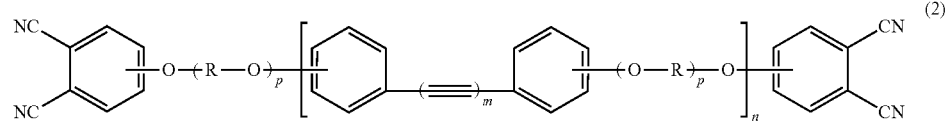

Also disclosed is a thermoset made by curing a composition comprising the above phthalonitrile monomer.

Also disclosed is a method comprising: reacting a diphenyl acetylene compound with an excess of an aromatic diol in the presence of an alkali metal carbonate to form the above oligomer.

Also disclosed is a method comprising: reacting a phenoxyphthalonitrile with an acetylene compound to form a phthalonitrile monomer having the formula below. The value m is as defined above.

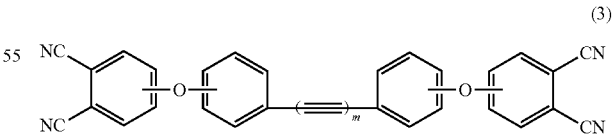

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
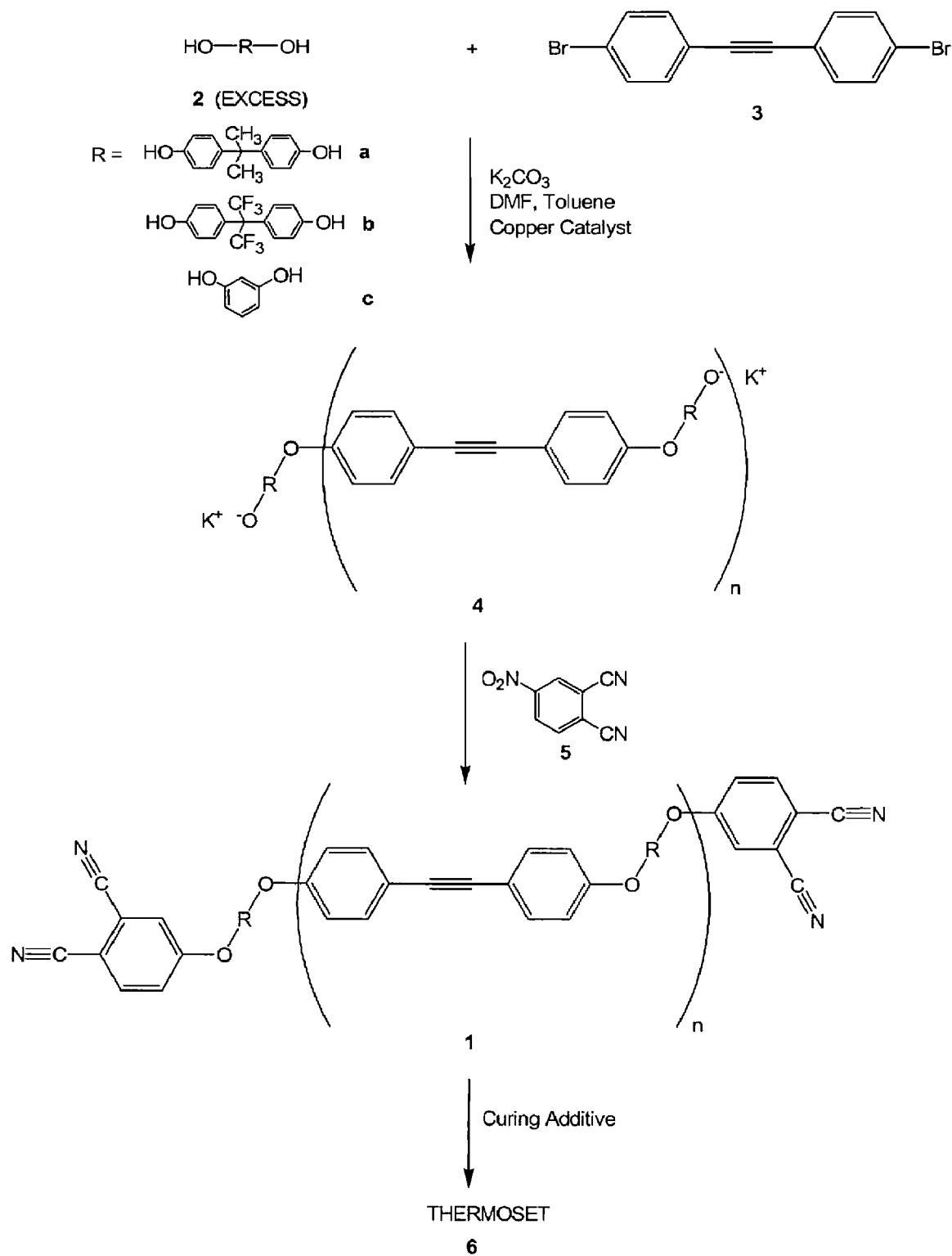
FIG. 1 shows a synthesis oligomer phthalonitrile monomer 1 and thermoset 6.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The present disclosure is targeted towards developing high temperature and flame resistant composites and addressing composite processability based on cost effective manufacturing techniques such as resin transfer molding (RTM), resin infusion molding, and filament winding. One objective has been concerned with the incorporation of units within the backbone to enhance the flammability resistance and thermo-oxidative properties while retaining low temperature processability. A low melt viscosity resin enables composite processing by resin transfer molding (RTM) and resin infusion methods. Furthermore, a low melt viscosity and a larger processing window are useful for fabrication of thick composite sections where the melt has to impregnate shaped thick fiber preforms.

This disclosure is related to the synthesis and polymerization of low melting phthalonitrile monomers containing multiple aromatic ether and alkynyl (acetylenic) moieties between the terminal phthalonitrile units, including oligomers thereof. The oligomeric aromatic ether-alkynyl-containing phthalonitrile monomers can polymerize stepwise through initially the phthalonitrile units and ultimately at higher temperature through the alkynyl groups found in the backbone to afford high temperature, flame resistant thermosets. In the absence of a curing additive for the phthalonitrile reaction, thermal treatment of the novel alkynyl-containing phthalonitriles to temperatures at about 350° C. may result in reaction only of the alkynyl units to a thermoset. Desirable physical properties such as retention of structural integrity (no glass transition temperature, $T_g$) at elevated temperatures and high thermal and oxidation stability can be obtained at lower postcure temperatures. Reaction of both reactive sites (phthalonitrile aid alkynyl units) can afford a highly crosslinked system. Polymeric composites and coatings formulated from the disclosed phthalonitriles may have outstanding thermo-oxidative and flammability properties for ship, submarine, and aerospace applications and may withstand continuous high temperatures (300-375° C.) in oxidative environments such as air for extended periods. The oligomeric phthalonitrile polymers may have melting points or glass transition temperatures between 50 and 100° C. with the polymerization occurring in excess of 200° C.

The use of low molecular weight precursor resins to obtain thermosetting polymeric materials with high thermo-oxidative properties may be advantageous from a processing standpoint. Precursor resins are useful in composite fabrication by a variety of methods such as resin infusion molding, resin transfer molding, filament winding and prepreg consolidation. The phthalonitriles may be suitable for numerous aerospace and electronic applications due to their potential thermal and oxidative properties, ease of processability, and low water absorption relative to other high temperature polymers such as polyimides. Furthermore, resins with a large window between the melting point and the cure temperature may be desirable to control the viscosity and the rate of curing. With the phthalonitrile monomers disclosed herein, processability to shaped composite components may be achieved in non-autoclave conditions potentially above 70° C. and by cost effective methods.

The synthesis of the thermoset may be performed in three steps. First, an aromatic diol is reacted with a diphenyl acetylene compound to form an oligomer. The diphenyl acetylene compound generally is terminated by halogen, such as Br or I. Suitable compounds include, but are not limited to, 4,4'-dibromodiphenylacetylene and 4,4'-dibromodiphenylbutadiyne. The diol may also be a hydroxy-terminated oligomer. Second, the oligomer is reacted with a 3- or 4-nitrophthalonitrile to make a phthalonitrile monomer. Third, the phthalonitrile monomer is cured to make a thermoset. These steps are shown in FIG. 1. Any reference to an ingredient can refer to one embodiment of such ingredient or a combination of one or more embodiments. All polymeric and oligomeric structures claimed include all configurations, isomers, and tacticities of the polymers and oligomers within the scope of the claims. The term "oligomer" as used herein does not place any upper or lower limit on the chain length of the oligomer and means that one or more compounds of the general formula are present with the average molecular weight dependent on the ratios of reactants.

The synthesis of a series of multiple aromatic ether-linked phthalonitriles 1, which contain arylene ether and alkynyl units in the backbone, has been achieved by a modified Ullmann reaction between bisphenol 2, 4,4'-dibromodiphenylacetylene 3, $K_2CO_3$, N,N-dimethylformamide (DMF), and toluene (FIG. 1). Sodium carbonate may also be used instead of potassium carbonate. This mixed solvent system can allow the azeotropic distillation of the water formed as a by-product in the reaction at temperatures between 135 and 145° C. The synthesis can be facilitated by the addition of a catalytic amount of a copper (I) complex (($PPh_3$)CuBr). Once no more water is observed being azeotropically distilled and infrared (IR) spectroscopy confirms the desired oligomeric product, the Ullmann reaction may be considered complete.

An excess of diol is used so that the oligomer is terminated by the diol in metal salt form. Suitable molar ratios of diol to phosphine oxide include, but are not limited to, 2:1, 3:2, 4:3, and 5:4. These ratios produce average values for n of 1, 2, 3, and 4 respectively. Equation (4) shows the product of bisphenol A and 4,4'-dibromodiphenylbutadiyne (m=2) in a 2:1 ratio. Equation (5) shows the product of resorcinol and 4,4'-dibromodiphenylacetylene (m=1) in a 3:2 ratio. The chain lengths shown represent the average length. The product generally contains a mixture of chain lengths.

(4)

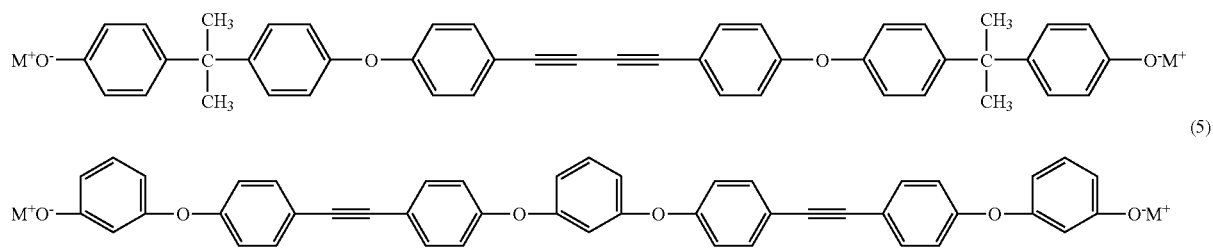

(5)

Further reaction of 4 with 4-nitrophthalonitrile 5 afforded the oligomeric phthalonitriles 1, which were readily soluble in common organic solvents such as toluene, DMF, acetone, methylene chloride, ether, and chloroform in 91-95% yields. The structure of the phthalonitrile monomers 1 was confirmed by IR and $^1$H-NMR spectroscopy. The length of the spacer between the terminal phthalonitrile groups can be varied by changing the ratio between 2 (excess) and 3. Oligomeric phthalonitrile resins 1 generally have melting points between 70 and 100° C. Several oligomeric phthalonitriles 1 have been synthesized by this method and the structures of 1a, 1b, and 1c are shown in Equations (6), (7), and (8) respectively.

(6)

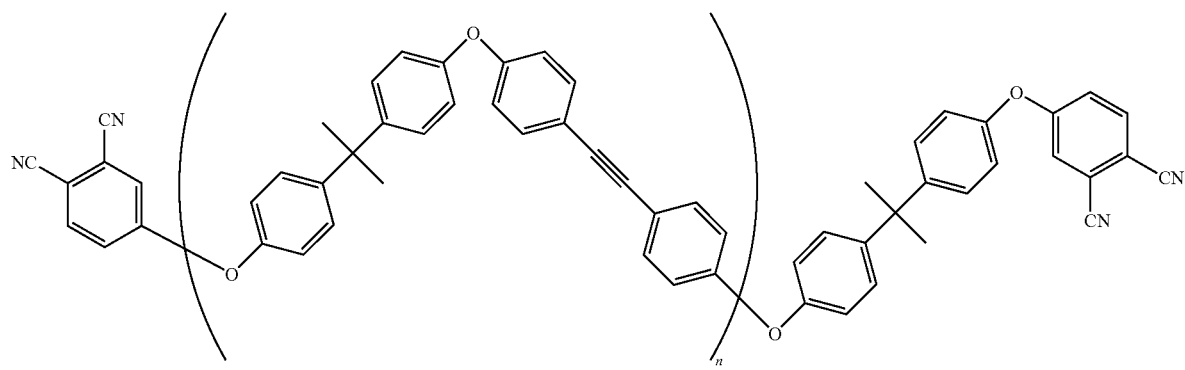

(7)

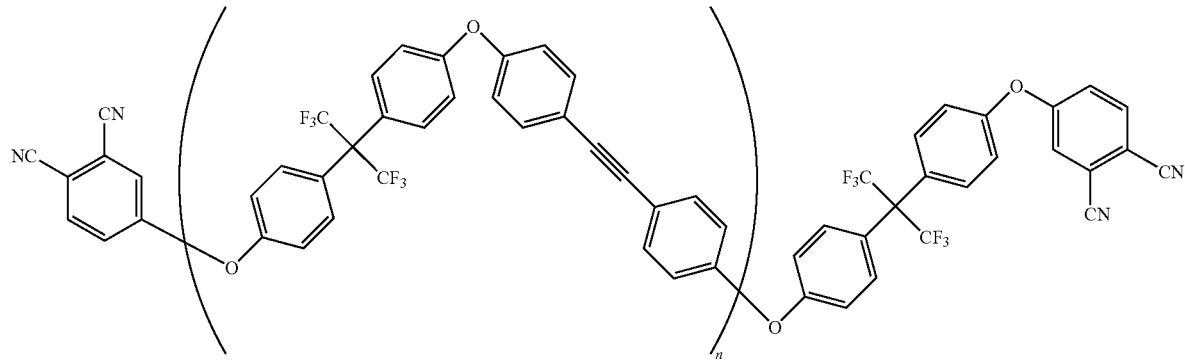

(8)

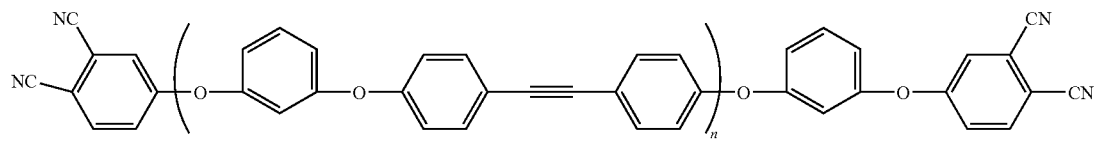

Typically, there is at least a 2:1 molar ratio of nitrophthalonitrile to oligomer to ensure that all terminal groups react with the nitrophthalonitrile. Any remaining unreacted terminal groups can make it more difficult to control the reaction during the curing step. Typically, the oligomer and the nitrophthalonitrile are dissolved in a solvent and heated. As above, the product generally contains a mixture of chain lengths.

Figure 2:
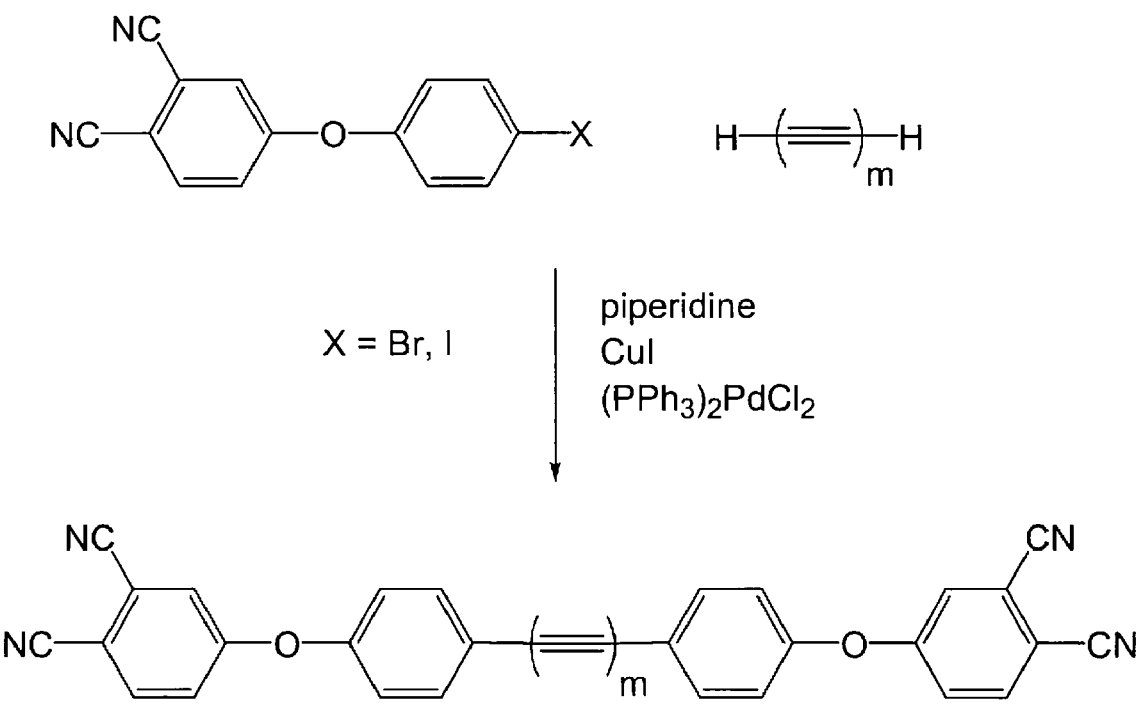
FIG. 2 shows an alternative synthesis of a phthalonitrile monomer.

In an alternative synthesis a phenoxyphthalonitrile is reacted with an acetylene compound to form the phthalonitrile monomer, as shown in FIG. 2. This synthesis produces a monomer with a single repeat unit of phenylacetylene (n=1) without the aryl ether moiety (p=0).

In the final step, a mixture comprising the phthalonitrile monomer and a curing agent is cured to form a thermoset. The cyano groups are the cure sites. As these groups react with the curing agent a cross-linked thermoset is formed. The mixture can comprise multiple phthalonitrile monomers having different R groups and different values of n.

The curing agent can be any substance useful in promoting the polymerization of the phthalonitrile monomer. More than one curing agent can be used. Typically, the same amount of curing agent can be used as conventionally used in curing analogous prior art monomers. Typically the curing agent is added to a melt of the phthalonitrile monomer with stirring. The mixture is then cured in one or more curing stages. Typical curing temperatures range from about 80° C. to about 500° C. More typically, the range is from 80° C. to about 375° C. Generally, more complete curing occurs at higher temperatures.

Suitable curing agents include, but are not limited to, aromatic amines, primary amines, secondary amines, diamines, polyamines, amine-substituted phosphazenes, phenols, strong acids, organic acids, strong organic acids, inorganic acids, metals, metallic salts, metallic salt hydrates, metallic compounds, halogen-containing aromatic amines, clays, and chemically modified clays. The use of clays or chemically modified clays may improve the mechanical and flammability properties of the thermoset. Typically, chemical modification of a clay involves replacing sodium ions with ammonium to form quarternary ammonium salts.

Specific curing agents include, but are not limited to, bis[4-(4-aminophenoxy)phenyl]sulfone (p-BAPS), bis[4-(3-aminophenoxy)phenyl]sulfone (m-BAPS), 1,4-bis(3-aminophenoxy)benzene (p-APB), 1,12-diaminododecane, diphenylamine, epoxy amine hardener, 1,6-hexanediamine, 1,3-phenylenediamine, 1,4-phenylenediamine, p-toluenesulfonic acid, cuprous iodide, cuprous bromide, 1,3-bis(3-aminophenoxy)benzene (m-APB), 3,3'-dimethyl-4,4'-diaminodiphenylsulfone, 3,3'-diethoxy-4,4'-diaminodiphenylsulfone, 3,3'-dicarboxy-4,4'-diaminodiphenylsulfone, 3,3'-dihydroxy-4,4'-diaminodiphenylsulfone, 3,3'-disulfo-4,4'-diaminodiphenylsulfone, 3,3'-diaminobenzophenone, 4,4'-diaminobenzophenone, 3,3'-dimethyl-4,4'-diaminobenzophenone, 3,3'-dimethoxy-4,4'-diaminobenzophenone, 3,3'-dicarboxy-4,4'-diaminobenzophenone, 3,3'-dihydroxy-4,4'-diaminobenzophenone, 3,3'-disulfo-4,4'-diaminobenzophenone, 4,4'-diaminodiphenyl ethyl phosphine oxide, 4,4'-diaminodiphenyl phenyl phosphine oxide, bis(3-aminophenoxy-4'-phenyl)phenyl phosphine oxide, methylene dianiline, hexakis(4-aminophenoxy)cyclotriphosphazene, 3,3'-dichloro-4,4'-diaminodiphenylsulfone, 2,2'-bis(trifluoromethyl)-4,4'-diaminobiphenyl, 2,2'-bis(4-aminophenyl)hexafluoropropane, bis[4-(4-aminophenoxy)phenyl]2,2'-hexafluoropropane, 1,1-bis(4-aminophenyl)-1-phenyl-2,2,2-trifluoroethane, 3,3'-dichloro-4,4'-diaminobenzophenone, 3,3'-dibromo-4,4'-diaminobenzophenone, aniline-2-sulfonic acid, 8-aniline-1-naphthalenesulfonic acid, benzene sulfonic acid, butylsulfonic acid, 10-camphorsulfonic acid, 2,5-diaminobenzenesulfonic acid, 6-dimethylamino-4-hydroxy-2-naphthalenesulfonic acid, 5-dimethylamino-1-naphthalenesulfonic acid, 4-hydroxy-3-nitroso-1-naphthalenesulfonic acid tetrahydrate, 8-hydroxyquinoline-5-sulfonic acid, methylsulfonic acid, phenylboric acid, 1-naphthalenesulfonic acid, 2-naphthalenesulfonic acid, 1,5-naphthalenedisulfonic acid, 2,6-naphthalenedisulfonic acid, 2,7-naphthalenedisulfonic acid, picrylsulfonic acid hydrate, 2-pyridineethanesulfonic acid, 4-pyridineethanesulfonic acid, 3-pyridinesulfonic acid, 2-pyridinylhydroxymethanesulfonic acid, sulfanilic acid, 2-sulfobenzoic acid hydrate, 5-sulfosalicylic acid hydrate, 2,4-xylenesulfonic acid, sulfonic acid containing dyes, organic phosphorus-containing acids, phenylphosphinic acid, diphenylphosphinic acid, propylphosphonic acid, 1-aminoethylphosphonic acid, 4-aminophenylphosphonic acid, butylphosphonic acid, t-butylphosphonic acid, 2-carboxyethylphosphonic acid, 2-chloroethylphosphonic acid, dimethylphosphonic acid, ethylphosphonic acid, methylenediphosphonic acid, methylphosphonic acid, phosphonoacetic acid, bis(hydroxymethyl) phosphonic acid, chloromethylphosphonic acid, di-n-butylphosphonic acid, dichloromethylphosphonic acid, diphenyldithiophosphonic acid, 1,2-ethylenediphosphonic acid, n-hystaderylphosphonic acid, hydroxymethylphosphonic acid, n-octadecylphosphonic acid, n-octylphosphonic acid, phenylphosphonic acid, propylenediphosphonic acid; n-tetradecylphosphonic acid, concentrated sulfuric acid, phenylphosphonic acid, copper, iron, zinc, nickel, chromium, molybdenum, vanadium, beryllium, silver, mercury, tin, lead, antimony, calcium, barium, manganese, magnesium, cobalt, palladium, platinum, statuous chloride, cuprous bromide, cuprous cyanide, cuprous ferricyanide, zinc chloride, zinc bromide, zinc iodide, zinc cyanide, zinc ferrocyanide, zinc acetate, zinc sulfide, silver chloride, ferrous chloride ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrates, stannous chloride dihydrate, aluminum nitrate hydrates, aluminum nitrate nonahydrate, triphenylphosphine oxide complex, montmorillonite, and chemically modified montmorillonite.

The mixture may also comprise 4,4'-bis(3,4-dicyanophenoxy)biphenyl, bis[4-(3,4-dicyanophenoxy)phenyl]dimethylmethane, bis[4-(2,3-dicyanophenoxy)phenyl]dimethylmethane, bis[4-(3,4-dicyanophenoxy)phenyl]bis(trifluoromethyl)methane, bis[4-(2,3-dicyanophenoxy)phenyl]bis(trifluoromethyl)methane, 1,3-bis(3,4-dicyanophenoxy)benzene, or 1,4-bis(3,4-dicyanophenoxy)benzene. These compounds are also phthalonitrile monomers. The mixture can also comprise any compound with one or more phthalonitrile groups. Typically, these phthalonitrile compounds have two or more phthalonitrile groups. Such phthalonitrile compounds include, but are not limited to, the phthalonitrile monomers disclosed in the patents cited above. All these compounds can cure with the phthalonitrile monomers of the present disclosure.

The phthalonitrile composition may also comprise an additional component to impart desirable structural or thermal properties. The monomer can be mixed with the additional component before curing. Suitable additional components include, but are not limited to, carbon nanotubes, clays, carbon nanofibers, metal oxides, zinc oxide, and combinations thereof.

Figure 3:
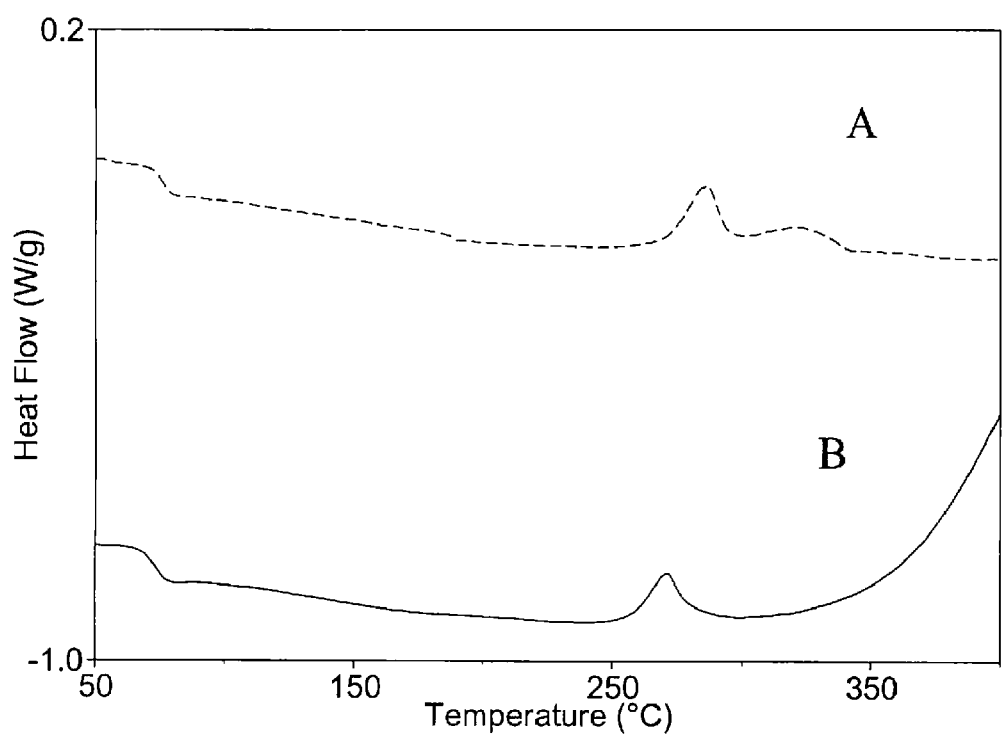
FIG. 3 shows DSC thermograms of previous phthalonitrile resin (top) and new phthalonitrile resin 1a (bottom) cured with 3% p-BAPS.

Polymerization studies of phthalonitrile 1 (n=1) were achieved by DSC analyses up to 400° C. in the presence of 3 weight % of bis(4-[4-aminophenoxy]phenyl)sulfone (p-BAPS) to afford thermosets 6. Using a previous oligomeric, low melting phthalonitrile monomer (Equation (9) as an example, the DSC thermogram (FIG. 3, plot A) revealed an endothermic transition (glass transition temperature, ($T_g$)) at approximately 75° C. and an exothermic transition peaking at 265° C. attributed to the reaction with p-BAPS. For 1a, an endothermic peaking transition ($T_g$) at about 70° C. and exothermic transitions peaking 260° C. and commencing above 300° C. were attributed to reaction of the phthalonitrile and alkynyl units, respectively (FIG. 3, plot B). Therefore, 1a exhibited low softening temperatures, was completely free flowing between 120 and 150° C. (as determined by a visual melting test), and had a long processing window (~100° C.) before reaction with the curing additive occurred. The polymerization studies of 1b and 1c displaced similar DSC thermograms as 1a.

the phthalonitrile-based polymers would be expected to exhibit improvements in specific physical properties when used at high temperatures or in a fire.

Having described the invention, the following examples are given to illustrate specific applications of the invention. These specific examples are not intended to limit the scope of the invention described in this application.

EXAMPLE 1

Synthesis of 2:1 oligomeric phthalonitrile based on bisphenol-A and 4,4'-dibromodiphenylacetylene—To a 100 mL, three-necked flask fitted with a thermometer, a Dean-Stark trap with condenser, and a nitrogen inlet were added bisphenol A (3.29 g, 14.4 mmol), 4,4'-dibromodiphenylacetylene (2.40 g, 7.14 mmol), (PPh$_3$)$_3$CuBr (0.1 g), powdered anhydrous K$_2$CO$_3$ (4.00 g, 29.0 mmol), toluene (5 mL), and N,N-dimethylformamide (DMF) (10 mL). The resulting mixture was degassed with argon at ambient temperature and the

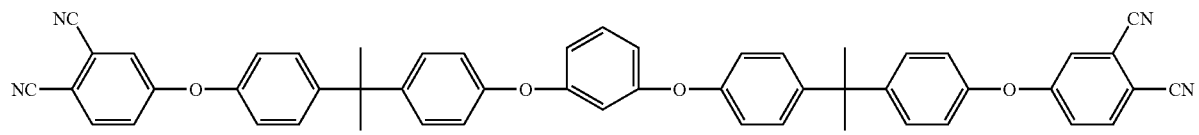

(9)

Low molecular weight diaryl ether alkynyl-containing compounds 4 were used in the preparation of oligomeric phthalonitriles 1. The oligomeric phthalonitriles 1 were easily converted to polymer 6 under thermal conditions and in the presence of a curing additive. At temperatures in excess of 350° C., the alkynyl units can commence to react to afford crosslinked polymeric materials. A thermoset formed from reaction of both the phthalonitrile and the alkynyl units may be highly crosslinked. In the absence of a curing additive for the reaction of the phthalonitrile units, the monomers 1 can be thermally cured through the alkynyl units yielding a conjugated carbon-carbon system with pendent aromatic ether phthalonitrile groups. Thus, depending on the curing conditions and thermal parameters, high temperature thermosetting materials, which would be expected to show physical properties relative to previous phthalonitriles, can be readily obtained and the polymerization reactions (phthalonitriles and alkyne) can be easily controlled.

Figure 4:
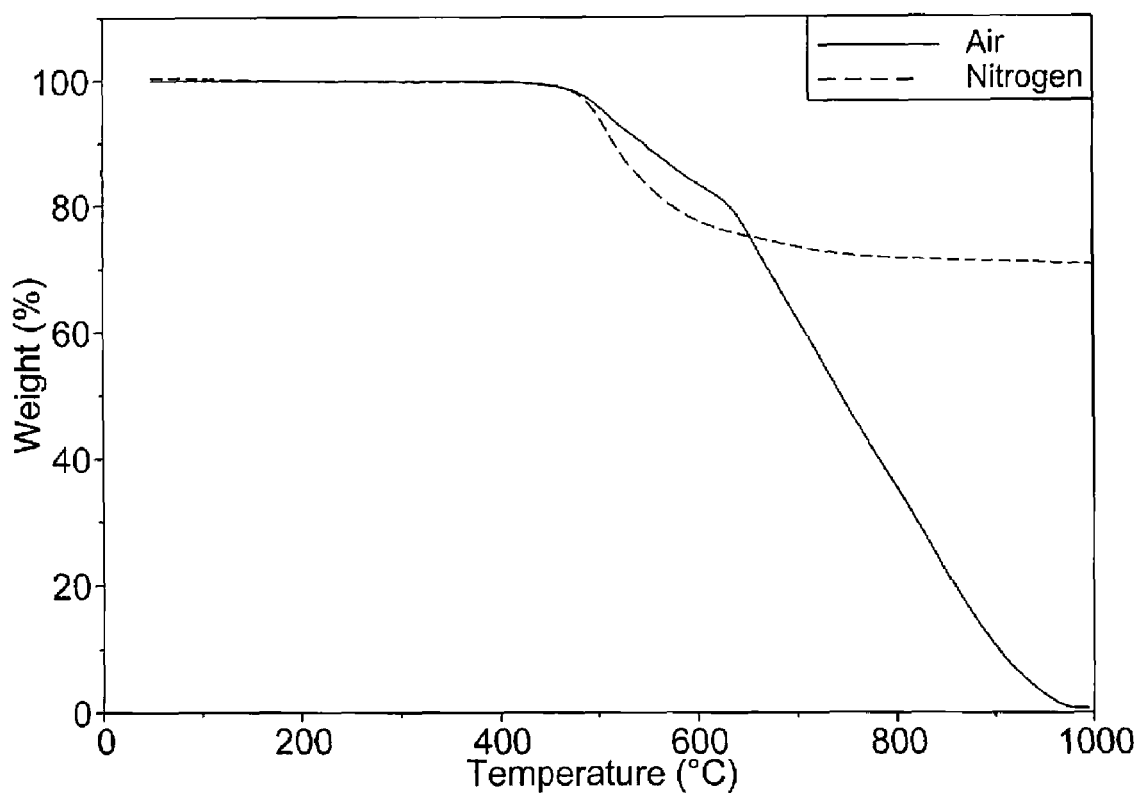
FIG. 4 shows TGA thermograms of bisphenol A alkynyl phthalonitrile resin 6a heated under air and nitrogen atmospheres.

Regardless of the curing conditions, the phthalonitrile monomer 1 may offer a broad processing window, which can be important for the fabrication of complex shaped composite components. The thermosets or cured polymers 6 can show improved thermo-oxidative properties. FIG. 4 shows TGA thermograms of the bisphenol A derived phthalonitrile thermoset 6a that has been heated to 1000° C. The polymer 6a exhibits thermal and oxidative stability to about 450° C. before any significant weight loss occurred. The viscosity of the polymerization system can be easily controlled for extended periods due to the large processing window, which is advantageous for the fabrication of complex composite components and device coatings. Due to the superb thermal and oxidative stability of phthalonitrile polymers 6 cured to 400° C., the materials have potential for a variety of applications (ship, aerospace, marine, and electronic) including its use in the fabrication of advanced composites by conventional prepreg consolidation, RTM, injection molding, filament winding, and as a coating for electronic devices. Thus, Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (2.51 g, 14.5 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (5.76 g, 90% yield). IR [cm$^{-1}$]: δ 3058 (C=CH), 2969 (CH$_3$), 2231 (CN), 2205 (alkyne), 1589 (C=C), 1491 (aromatic), 1281 (CH$_3$), 1248 (C—O), 1173 (C—O), 970 (C—O), 834 (aromatic).

EXAMPLE 2

Curing of 2:1 oligomeric phthalonitrile based on bisphenol-A and 4,4'-dibromodiphenylacetylene with an aromatic amine—Samples containing the 2:1 oligomeric phthalonitrile from example 1 and 2-3 weight % of bis(4-[4-aminophenoxy]phenyl)sulfone (p-BPAS) or 1,3-bis(3-aminophenoxy) benzene (m-APB) were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 450° C. in air.

EXAMPLE 3

Selective curing of 2:1 oligomeric phthalonitrile based on bisphenol-A and 4,4'-dibromodiphenylacetylene by selective crosslinking of alkyne units—Samples containing the 2:1 oligomeric phthalonitrile from Example 1 were cured under nitrogen by heating at 270° C. for 4 h, 300° C. for 4 h, 350° C. for 4 h, and 375° C. for 8 h to afford a polymer from reaction only of the alkyne units. The polymers exhibited excellent thermal and oxidative stability up to 425° C. before any weight loss was detected. Catastrophic decomposition occurred after 450° C. in air.

EXAMPLE 4

Selective low temperature curing of 2:1 oligomeric phthalonitrile based on bisphenol-A and 4,4'-dibromodiphenylacetylene with an aromatic amine to crosslink only the phthalonitrile units—Samples containing the 2:1 oligomeric phthalonitrile from Example 1 and 2-3 weight % of p-BAPS or m-APB were stirred at 200° C. for 2 minutes and cured under nitrogen by heating at 270° C. for 12 h (overnight) to afford a polymer from reaction only of the phthalonitrile units. The alkyne units had not reacted. The polymers exhibited good thermal and oxidative stability up to 300° C. before any weight loss was detected. Catastrophic decomposition occurred after 350° C. in air.

EXAMPLE 5

Curing of phthalonitrile crosslinked 2:1 oligomeric phthalonitrile based on bisphenol-A and 4,4'-dibromodiphenylacetylene to further crosslink alkyne units—Crosslinked samples containing the 2:1 oligomeric phthalonitrile from Example 4 and 2-3 weight % of p-BAPS or 771-APB were further heated at 300° C. for 4 h, 350° C. for 4 h, and 375° C. for 8 h to afford a polymer by crosslinking of the alkyne units. The polymers exhibited good thermal and oxidative stability up to 400° C. before any weight loss was detected. Catastrophic decomposition occurred after 450° C. in air.

EXAMPLE 6

Synthesis of 2:1 oligomeric phthalonitrile based on resorcinol and 4,4'-dibromodiphenylacetylene—To a 100 mL, three-necked flask fitted with a thermometer, a Dean-Stark trap with condenser, and a nitrogen inlet were added resorcinol (3.64 g, 33.1 mmol), 4,4'-dibromodiphenylacetylene (4.00 g, 11.9 mmol), $(PPh_3)_3CuBr$ (0.1 g), powdered anhydrous $K_2CO_3$ (5.00 g, 36.2 mmol), toluene (10 mL), and DMF (3 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (5.08 g, 29.3 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (6.36 g, 67% yield). IR $[cm^{-1}]$: δ 3075 (C═CH), 2232 (CN), 2207 (alkyne), 1585 (C═C), 1477 (aromatic), 1308 (aromatic), 1244 (C—O), 1172 (C—O), 975 (C—O), 837 (aromatic).

EXAMPLE 7

Curing of 2:1 oligomeric phthalonitrile based on resorcinol and 4,4'-dibromodiphenylacetylene with an aromatic amine—Samples containing the 2:1 oligomeric phthalonitrile from Example 6 and 2-3 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. Under the curing conditions, the phthalonitrile and alkyne units reacted. The polymers exhibited excellent thermal and oxidative stability up to 450° C. before any weight loss was detected. Catastrophic decomposition occurred after 500° C. in air.

EXAMPLE 8

Selective curing of 2:1 oligomeric phthalonitrile based on resorcinol and 4,4'-dibromodiphenylacetylene by selective crosslinking of alkyne units—Samples containing the 2:1 oligomeric phthalonitrile from Example 6 were cured under nitrogen by heating at 270° C. for 4 h, 300° C. for 4 h, 350° C. for 4 h, and 375° C. for 8 h to afford a polymer from reaction only of the alkyne units. The polymers exhibited excellent thermal and oxidative stability up to 425° C. before any weight loss was detected. Catastrophic decomposition occurred after 450° C. in air.

EXAMPLE 9

Selective low temperature curing of 2:1 oligomeric phthalonitrile based on resorcinol and 4,4'-dibromodiphenylacetylene with an aromatic amine to crosslink only the phthalonitrile units—Samples containing the 2:1 oligomeric phthalonitrile from Example 6 and 2-3 weight % of p-BAPS or m-APB were stirred at 200° C. for 2 minutes and cured under nitrogen by heating at 270° C. for 12 h (overnight) to afford a polymer from reaction only of the phthalonitrile units. The alkyne units had not reacted. The polymers exhibited good thermal and oxidative stability up to 325° C. before any weight loss was detected. Catastrophic decomposition occurred after 375° C. in air.

EXAMPLE 10

Curing of phthalonitrile crosslinked 2:1 oligomeric phthalonitrile based on resorcinol and 4,4'-dibromodiphenylacetylene to further crosslink alkyne units—Crosslinked samples containing the 2:1 oligomeric phthalonitrile from Example 9 and 2-3 weight % of p-BAPS or m-APB were further heated at 300° C. for 4 h, 350° C. for 4 h, and 375° C. for 8 h to afford a polymer by crosslinking of the alkyne units. The polymers exhibited good thermal and oxidative stability up to 425° C. before any weight loss was detected. Catastrophic decomposition occurred after 450° C. in air.

EXAMPLE 11

Synthesis of 2:1 oligomeric phthalonitrile based on bisphenol A6F and 4,4'-dibromodiphenylacetylene—To a 100 mL, three-necked flask fitted with a thermometer, a Dean-Stark trap with condenser, and a nitrogen inlet were added bisphenol A6F (8.10 g, 24.1 mmol), 4,4'-dibromodiphenylacetylene (4.00 g, 11.9 mmol), $(PPh_3)_3CuBr$ (0.2 g), powdered anhydrous $K_2CO_3$ (5.00 g, 36.2 mmol), toluene (10 mL), and DMF (40 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (4.71 g, 27.2 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (12.05 g, 91% yield). IR [$cm^{-1}$]: δ 3075 (C═CH), 2232 (CN), 2205 (alkyne), 1585 (C═C), 1477 (aromatic), 1308 (aromatic), 1244 (C—O), 1172 (C—O), 975 (C—O), 837 (aromatic).

EXAMPLE 12

Curing of 2:1 oligomeric phthalonitrile based on bisphenol-A6F and 4,4'-dibromodiphenylacetylene with an aromatic amine—Samples containing the 2:1 oligomeric phthalonitrile from Example 11 and 2-3 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. Under the curing conditions, the phthalonitrile and alkyne units reacted. The polymers exhibited excellent thermal and oxidative stability up to 450° C. before any weight loss was detected. Catastrophic decomposition occurred after 500° C.

EXAMPLE 13

Selective curing of 2:1 oligomeric phthalonitrile based on bisphenol-A6F and 4,4'-dibromodiphenylacetylene by selective crosslinking of alkyne units—Samples containing the 2:1 oligomeric phthalonitrile from Example 11 were cured under nitrogen by heating at 270° C. for 4 h, 300° C. for 4 h, 350° C. for 4 h, and 375° C. for 8 h to afford a polymer from reaction only of the alkyne units. The polymers exhibited excellent thermal and oxidative stability up to 415° C. before any weight loss was detected. Catastrophic decomposition occurred after 450° C. in air.

EXAMPLE 14

Selective low temperature curing of 2:1 oligomeric phthalonitrile based on bisphenol-A6F and 4,4'-dibromodiphenylacetylene with an aromatic amine to crosslink only the phthalonitrile units—Samples containing the 2:1 oligomeric phthalonitrile from Example 11 and 2-3 weight % of p-BAPS or m-APB were stirred at 200° C. for 2 minutes and cured under nitrogen by heating at 270° C. for 12 h (overnight) to afford a polymer from reaction only of the phthalonitrile units. The alkyne units had not reacted. The polymers exhibited good thermal and oxidative stability up to 315° C. before any weight loss was detected. Catastrophic decomposition occurred after 375° C. in air.

EXAMPLE 15

Curing of phthalonitrile crosslinked 2:1 oligomeric phthalonitrile based on bisphenol-A6F and 4,4'-dibromodiphenylacetylene to further crosslink alkyne units—Crosslinked samples containing the 2:1 oligomeric phthalonitrile from Example 14 and 2-3 weight % of p-BAPS or m-APB were further heated at 300° C. for 4 h, 350° C. for 4 h, and 375° C. for 8 h to afford a polymer by crosslinking of the alkyne units. The polymers exhibited good thermal and oxidative stability up to 425° C. before any weight loss was detected. Catastrophic decomposition occurred after 450° C. in air.

EXAMPLE 16

Synthesis of 2:1 oligomeric phthalonitrile based on biphenol and 4,4'-dibromodiphenylacetylene—To a 250 mL, three-necked flask fitted with a thermometer, a Dean-Stark trap with condenser, and a nitrogen inlet were added 4,4'-biphenol (10.0 g, 53.7 mmol), 4,4'-dibromodiphenylacetylene (8.93 g, 26.6 mmol), $(PPh_3)_3CuBr$ (0.3 g), powdered anhydrous $K_2CO_3$ (11.1 g, 80.6 mmol), toluene (20 mL), and DMF (100 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (9.32 g, 53.9 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (19.2 g, 90% yield). IR [$cm^{-1}$]: δ 3075 (C═CH), 2232 (CN), 2202 (alkyne), 1585 (C═C), 1477 (aromatic), 1310 (aromatic), 1243 (C—O), 1172 (C—O), 977 (C—O), 837 (aromatic).

EXAMPLE 17

Curing of 2:1 oligomeric phthalonitrile based on biphenol and 4,4'-dibromodiphenylacetylene with an aromatic amine—Samples containing the 2:1 oligomeric phthalonitrile from Example 16 and 2-3 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. Under the curing conditions, the phthalonitrile and alkyne units reacted. The polymers exhibited excellent thermal and oxidative stability up to 480° C. before any weight loss was detected. Catastrophic decomposition occurred after 500° C. in air.

EXAMPLE 18

Synthesis of 5:4 oligomeric phthalonitrile based on bisphenol-A and 4,4'-dibromodiphenylacetylene—To a 100 mL, three-necked flask fitted with a thermometer, a Dean-Stark trap with condenser, and a nitrogen inlet were added bisphenol A (5.00 g, 21.9 mmol), 4,4'-dibromodiphenylacetylene (5.88 g, 17.5 mmol), $(PPh_3)_3CuBr$ (0.1 g), powdered anhydrous $K_2CO_3$ (7.55 g, 54.7 mmol), toluene (10 mL), and DMF (50 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (1.57 g, 9.00 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 5:4 oligomeric phthalonitrile (10.5 g, 92% yield). IR $[cm^{-1}]$: δ 3058 (C=CH), 2969 ($CH_3$), 2231 (CN), 2205 (alkyne), 1589 (C=C), 1491 (aromatic), 1281 ($CH_3$), 1248 (C—O), 1173 (C—O), 970 (C—O), 834 (aromatic).

EXAMPLE 19

Curing of 5:4 oligomeric phthalonitrile based on bisphenol-A and 4,4'-dibromodiphenylacetylene with an aromatic amine—Samples containing the 2:1 oligomeric phthalonitrile from Example 18 and 4 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 450° C. in air.

EXAMPLE 20

Synthesis of 2:1 oligomeric phthalonitrile based on bisphenol-A and 3,3'-dibromodiphenylacetylene—To a 100 mL, three-necked flask fitted with a thermometer, a Dean-Stark trap with condenser, and a nitrogen inlet were added bisphenol A (5.00 g, 21.9 mmol), 3,3'-dibromodiphenylacetylene (3.64 g, 10.8 mmol), $(PPh_3)_3CuBr$ (0.1 g), powdered anhydrous $K_2CO_3$ (4.53 g, 32.8 mmol), toluene (5 mL), and DMF (30 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (3.81 g, 22.0 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (8.70 g, 90% yield). IR $[cm^{-1}]$: δ 3058 (C=CH), 2969 ($CH_3$), 2231 (CN), 2207 (alkyne), 1589 (C=C), 1491 (aromatic), 1281 ($CH_3$), 1248 (C—O), 1173 (C—O), 970 (C—O), 834 (aromatic).

EXAMPLE 21

Curing of 2:1 oligomeric phthalonitrile based on bisphenol-A and 3,3'-dibromodiphenylacetylene with an aromatic amine—Samples containing the 2:1 oligomeric phthalonitrile from Example 20 and 3 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 450° C. in air.

EXAMPLE 22

Formulation of carbon nanotubes with a 2:1 oligomeric phthalonitrile based on bisphenol-A and 4,4'-dibromodiphenylacetylene in a solvent—To a mixture of the 2:1 oligomeric phthalonitrile from Example 1 in a polar solvent, such as acetone, methylene chloride, or DMF, was added various amounts of carbon nanotubes (0.01 to 20 weight %). The mixture was thoroughly mixed. The solvent was removed and the mixture was heated and degassed at 200° C. Then 3 weight % of p-BAPS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric compositions exhibited excellent thermal and oxidative stability up to 425-450° C. before any weight loss was detected. Catastrophic decomposition occurred after 500° C. in air.

EXAMPLE 23

Formulation of clay with a 2:1 oligomeric phthalonitrile based on bisphenol-A and 4,4'-dibromodiphenylacetylene in a solvent—To a mixture of the 2:1 oligomeric phthalonitrile from Example 1 in an appropriate solvent was added various amount of clay (hydrated aluminum silicate) (0.01 to 20 weight %). The resulting mixtures were thoroughly mixed. The solvent was removed and the mixture heated and degassed at 200° C. Then 3-4 weight % of p-BAPS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 430-460° C. before any weight loss was detected. Catastrophic decomposition occurred after 500° C. in air.

EXAMPLE 24

Formulation of carbon nanofibers with a 2:1 oligomeric phthalonitrile based on bisphenol-A and 4,4'-dibromodiphenylacetylene in a solvent—To a mixture of the 2:1 oligomeric phthalonitrile from Example 1 in an appropriate solvent was added various amounts of carbon nanofibers (0.01 to 20 weight %). The mixtures were thoroughly mixed by stirring. The solvent was removed and the mixture heated and degassed at 200° C. Then 4 weight % of p-BAPS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 425-450° C. before any weight loss was detected. Catastrophic decomposition occurred after 500° C. in air.

EXAMPLE 25

Formulation of a metal oxide with 2:1 oligomeric phthalonitrile based on bisphenol-A and 4,4'-dibromodiphenylacetylene in a solvent—To a mixture of the 2:1 oligomeric phthalonitrile from Example 1 in an appropriate solvent was added various amount of powdered zinc oxide (0.01 to 20 weight %) with thorough mixing. The solvent was removed and the mixture heated and degassed at 200° C. Then 4-5 weight % of p-BAPS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before a weight loss was detected. Catastrophic decomposition occurred after 500° C. in air.

EXAMPLE 26

Formulation of clay with a 2:1 oligomeric phthalonitrile based on bisphenol-A and 4,4'-dibromodiphenylacetylene by physical mixing—To the 2:1 oligomeric phthalonitrile from Example 1 was added various amount of clay (hydrated aluminum silicate) (0.01 to 20 weight %). Thorough mixing was followed by degassed at 200° C. Then 3-5 weight % of p-BAPS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before a weight loss was detected. Catastrophic decomposition occurred after 500° C. in air.

EXAMPLE 27

Synthesis of phthalonitrile based on 4,4'-dibromodiphenyl-acetylene and 4-(4-iodo-phenoxy)phthalonitrile—To a 250 mL Schlenk flask under nitrogen was added 4-(4-iodophenoxy) phthalonitrile (8.15 g, 23.5), piperidine (14 mL), CuI (0.1 g), and $(PPh_3)_2PdCl_2$ (0.05 g). The mixture was frozen using liquid nitrogen and the flask evacuated using a vacuum pump. The flask was backfilled with acetylene (264 mL) and stirred at room temperature overnight (18 h) at which time a thick white precipitate formed. The contents were dumped into water (100 mL) and filtered using a Büchner funnel. The solid was washed with water until neutral and dried to yield (8.71 g, 80%) of a white solid. IR $[cm^{-1}]$: δ 3058 (C═CH), 2231 (CN), 2205 (alkyne), 1589 (C═C), 1491 (aromatic), 1248 (C-0), 1173 (C-0), 970 (C-0), 834 (aromatic).

EXAMPLE 28

Curing of 2:1 oligomeric phthalonitrile based on 4,4'-dibromodiphenyl-acetylene and 4-(4-iodo-phenoxy)phthalonitrile with an aromatic amine—Samples containing the 2:1 oligomeric phthalonitrile from Example 27 and 2-3 weight % of p-BAPS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 450° C. in air.

EXAMPLE 29

Synthesis of 2:1 oligomeric phthalonitrile based on bisphenol-A and 4,4'-dibromodiphenylbutadiyne—To a 100 mL, three-necked flask fitted with a thermometer, a Dean-Stark trap with condenser, and a nitrogen inlet were added bisphenol A (4.00 g, 17.5 mmol), 4,4'-dibromodiphenylbutadiyne (3.12 g, 8.67 mmol), $(PPh_3)_3CuBr$ (0.1 g), powdered anhydrous $K_2CO_3$ (4.51 g, 32.8 mmol), toluene (5 mL), and DMF (10 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and monitor the formation of the desired oligomeric product. Toluene was then removed by distillation and the reaction mixture was cooled to 50° C. At this time, 4-nitrophthalonitrile (3.29 g, 20.2 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric phthalonitrile (8.15 g, 90% yield). IR $[cm^{-1}]$: δ 3058 (C═CH), 2969 ($CH_3$), 2231 (CN), 2205, 2207 (alkyne), 1589 (C═C), 1491 (aromatic), 1281 ($CH_3$), 1248 (C—O), 1173 (C—O), 970 (C—O), 834 (aromatic).

EXAMPLE 30

Curing of 2:1 oligomeric phthalonitrile based on bisphenol-A and 4,4'-dibromodiphenylbutadiyne with an aromatic amine—Samples containing the 2:1 oligomeric phthalonitrile from Example 29 and 2-3 weight % of p-BAPS or m-APB were stirred at 200° C. for 2 minutes and cured under nitrogen by heating at 270° C. for 12 h (overnight), 300° C. for 4 b, 350° C. for 4 h, and 375° C. for 8 h to afford a polymer. The mixture began polymerization around 250° C. (crosslinking of phthalonitrile units) and was fully cured above 350° C. (crosslinking of butadiyne units). The polymers exhibited excellent thermal and oxidative stability up to 425° C. before any weight loss was detected. Catastrophic decomposition occurred after 450° C. in air.

EXAMPLE 31

Self-curing of 2:1 oligomeric phthalonitrile based on bisphenol-A and 4,4'-dibromodiphenylbutadiyne—Samples containing the 2:1 oligomeric phthalonitrile from Example 29 were cured by heating at 325° C. for 12 h (overnight) to react or crosslink the butadiyne units and afford a polymer without reaction of the phthalonitrile units. The polymers exhibited good thermal and oxidative stability up to 400° C. before any weight loss was detected. Catastrophic decomposition occurred after 450° C. in air.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A compound having the formula:

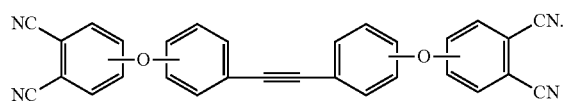

2. A thermoset made by curing a composition comprising a phthalonitrile monomer having the formula:

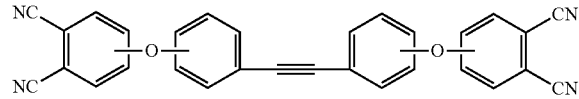

3. A method comprising:
reacting a phenoxyphthalonitrile with an acetylene compound to form a phthalonitrile monomer having the formula:

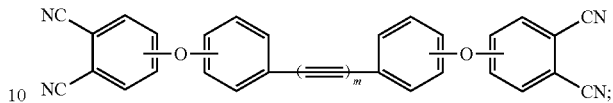

wherein m is a positive integer.

4. The method of claim 3, further comprising:
curing a composition comprising the phthalonitrile monomer.

5. The method of claim 4, further comprising:
the curing forms crosslinked alkynyl groups.

6. The method of claim 4,
wherein the composition comprises a curing agent; and
wherein the curing agent is a phthalonitrile curing agent, an aromatic amine, bis(4-[4-aminophenoxy]phenyl)sulfone, 1,3-bis(3-aminophenoxy)benzene, or a combination thereof.

* * * * *